US006258847B1

(12) United States Patent
Chachoua

(10) Patent No.: US 6,258,847 B1
(45) Date of Patent: *Jul. 10, 2001

(54) USE OF 2-MERCAPTOETHANOLAMINE (2-MEA) AND RELATED AMINOTHIOL COMPOUNDS AND COPPER(II)-3,5 DI-ISOPROPYL SALICYLATES AND RELATED COMPOUNDS IN THE PREVENTION AND TREATMENT OF VARIOUS DISEASES

(76) Inventor: Samir Chachoua, 28 Kangaroo Road, Murrembeena (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/719,908

(22) Filed: Sep. 25, 1996

(51) Int. Cl.$^7$ .................................................. A61K 31/195
(52) U.S. Cl. .............................................. 514/562
(58) Field of Search ............................................. 514/562

(56) References Cited

PUBLICATIONS

Brem et al 114 CA 183046j, 1991.*
Shiraki et al 92 CA 22517a, 1980.*
Apffel et al 82 CA 164694, 1975.*
Abramowitz et al 93 CA: 230648, 1980.*
Alberto Bergamini et al.—Cystamine Potently Suppresses In Vitro HIV Replication in Acutely and Chronically Infected Human Cells; The American Society for Clinical Investigation, Inc. 1994.
M.F.M.A. Smeets et al.—Differential Repair of Radiation–Induced DNA Damage in Cells of Human Squamous Cell Carcinoma and the Efect of Caffiene and Cysteamine of Induction and Repair of DNA Double–Strand Breaks; Radiation Research Society, 1994.
D. Becker et al.—Influence of Oxygen On The Repair Of direct Radiation Damage To DNA by Thiols In Model Systems; Int. J. Radiat. Biol., 1994, vol. 65, No. 5, 537–548.

Thomas M. Jeitner et al.—Thiol–Bearing Compounds Selectively Inhibit Protein Kinase C–Dependent Oxidative Events and Proliferation In Human T Cells; Elsevier Science B.V. 1994.
Takashi Iwashina et al.—The Synthesis of N–Acetyl–4–S–Cysteaminyl [U–14C]Phenol As A basis For The Development Of A Antimelanoma and Melanoma–Radio-imaging Agent; Appl. Radiol. vol. 45, No. 6, pp. 700–705, 1994.
E. Erciyas et al.—Antimicrobial Evaluation of Some Styryl Ketone Derivatives and Related Thiol Adducts; Journal of Pharmaceutical Sciences vol. 83, No. 4, Apr. 1994.
Anthony D. Keefe et al.—A Possible Prebiotic Synthesis of Pantethelne, A Precursor to Coenzyme A; Nature, vol. 373, Feb. 23, 1995.
S.D. Goldman et al.—Biochimica et Biophysica Acra 1203, 1995 114–122.
George R. Hoffmann et al.—Enhancement of the Activity of Blemomycin by Cysteamine in a Micronucleus Assay in G0 Human Lymphocytes; Elsevier Science Ireland ltd. 1995.
Jun–Ichi Ueda et al.—Reactions of Copper (II)–Oligopeptide Complexes with Hydrogen Peroxide: Effects of Biological Reductants; Free Radical Biology & Medicine, vol. 18, No. 5 pp. 929–933, 1995.
Kurt G. Hofer et al.—Low–LET and High LET Radiation Action of 1251 Decays in DNA; Effect of Cysteamine on Micronucleus Formation and Cell Killing; Radiation Research 141, 183–192 (1995).

* cited by examiner

Primary Examiner—Russell Travers
(74) Attorney, Agent, or Firm—Ted W. Whitlock

(57) ABSTRACT

New therapeutic compositions and applications of 2-mercaptoethanolamine (2-MEA) and related aminothiols and copper(II)-3,5 di-isopropyl salicylates, solely or in combination with other factors, agents, or processes that are physical, chemical and/or biological based are disclosed. These include precursors, intermediates, end products, catalysts, promoters and/or any factors, agents, or processes involved directly or indirectly from initial application of the compositions to the final result.

4 Claims, No Drawings

USE OF 2-MERCAPTOETHANOLAMINE (2-MEA) AND RELATED AMINOTHIOL COMPOUNDS AND COPPER(II)-3,5 DI-ISOPROPYL SALICYLATES AND RELATED COMPOUNDS IN THE PREVENTION AND TREATMENT OF VARIOUS DISEASES

BACKGROUND OF THE INVENTION

The present invention is directed to new therapeutic compositions and applications of 2-mercaptoethanolamine (2-MEA) and related aminothiols and di-isopropyl salicylates, solely or in combination with other factors, agents, or processes that are physical, chemical and/or biological based, including precursors, intermediates, end products, catalysts, promoters and/or any factors, agents, or processes involved directly or indirectly from initial application of the therapy to the final result. More particularly, the present invention is directed to the use of 2-MEA and related aminothiols and copper(II)-3,5 di-isopropyl salicylate in the treatment and prevention of AIDS, cancer, autoimmune disease, microbiological infections, and other diseases where immunological dysfunction and/or free radical formation function as part of the disease mechanism.

2-MEA has long been used by itself in the treatment of kidney disease, known as cysteinuria, where it may protect renal function. 2-MEA and related compounds have also been used as radiation protective agents in various formulations. This is at least due in part to the powerful antioxidant properties of these compounds. 2-MEA has also been linked with ulcerogenic properties in animal experiments. 2-MEA has been shown to exert both immunostimulant and immunomodulant action in in vitro trials. Jeitner et al., Biochimica et Biophysica Acta 1223:15–22 (1994). Cystamine, a related compound, has demonstrated in vitro inhibition of HIV. Bergamini et al., J. Clin. Invest. 93:2251–2257 (1994). Other applications of 2-MEA have been in the field of non-specific vitamin supplementation as a general antioxidant supplement in Swedish Anti-Aging Formula 223.

SUMMARY OF THE INVENTION

The antioxidant abilities of 2-MEA and related aminothiols make these compounds a valuable therapeutic adjunct to the treatment of any disease condition which directly or indirectly generates or causes the generation of free radicals. Essentially, this includes virtually every known disease condition as well as other conditions which may not be commonly regarded as diseases, as well as conditions which may be predisposed to or function as pre-cursors to disease. Although it is contemplated that the present invention include all such applications singly or in combination with other traditional therapies, there are several disease conditions where the application has produced significant results with the use of 2-MEA singly, or in combination with other factors, agents and/or processes. These diseases include AIDS, cancer, autoimmune disease, microbiological infections, and other diseases where immunological dysfunction and/or free radical formation function as part of the disease mechanism.

In the present invention, 2-MEA and related aminothiols are used in cancer prevention and treatment as a general immunostimulant and/or as an antioxidant to offset some of the toxic sequelae of the disease condition or other conventional therapies such as chemotherapy and radiotherapy. It is important in the application of 2-MEA and related aminothiols to either bind the compound to a delivery system which directs its protective action preferentially to healthy cells and/or time its delivery so as not to interfere with the anticancer activity of the therapy. A therapy may be beneficial to the body and antagonistic to the disease if timed correctly. If antioxidants like 2-MEA, for example, are timed correctly so as to inhibit or otherwise interfere with agents used in therapy which generate free radicals, then the previously antagonistic therapy may now protect disease by interfering with therapy and may now be classified as synergistic.

Application to autoimmune and immunodeficient conditions is indicated by the immunoregulating and immunomodulating activity demonstrated by 2-MEA. 2-MEA and related aminothiols including penicillamine and/or copper (II)-3,5-di-isopropyl salicylate were administered to patients as single agents, or in combination with other factors, agents, or processes which induced, stimulated, and/or facilitated their efficacy, or inhibited, suppressed or neutralized their toxic or undesired effects. Some agents and factors may have dual capabilities.

Although 2-MEA and related aminothiols may be incorporated in many uses requiring its antioxidant capabilities of other properties, the present invention is directed primarily to the medical applications of 2-MEA. The use of 2-MEA in the present invention impacts on diseases as varied as AIDS, systemic lupus erythromatosus, cancer, arthritis, autoimmune diseases, and can be used in sunscreens to minimize radiation damage.

Cimetidine, for example, may directly aid in the immunostimulating or immunomodulating action of 2-MEA while inhibiting ulcer formation. Copper(II)-3,5 di-isopropyl salicylate directly supports the antioxidant ability of 2-MEA while indirectly assisting in the treatment of cancer, for example, by having its own anti-cancer activity.

A therapeutic composition and method is disclosed for using 2-MEA and related aminothiols in the treatment and prevention of AIDS, cancer, autoimmune diseases, and microbiological infections, comprising the step of administering an effective dosage of a therapeutic composition comprising 2-MEA or related aminothiols to a patient having AIDS, cancer, autoimmune disease, microbiological infections, and other diseases where immunological dysfunction and/or free radical formation function as part of the disease mechanism. The effective dosage of 2-MEA or related aminothiols for administration to a patient is between approximately 0.01 mg and about 500 mg, at least once daily, up to four times a day. However, benefits may be achieved with a single dose, a monthly dose or a weekly dose. However, 2-MEA efficacy is best sustained with a daily dosage. The therapeutic composition is administered to a patient by a means selected from the group consisting of oral administration, catheter administration, intramuscular administration, intravenous administration, intradermal administration, intradural administration, intravesical administration, intraurethral administration, intrathecal administration, inhalation, topical administration, subcutaneous administration, and rectal administration or any other means of administration. The composition is orally administered in a form selected from the group consisting of a capsule, gel cap, liquid, tablet.

In yet another method of the present invention, 2-MEA and related aminothiols were combined with a living biological delivery system. 2-MEA or related aminothiols were incubated with a living biological system to form a mixture. The mixture was centrifuged to produce a pellet comprising the 2-MEA, the active ingredient, bound with the living biological system. The pellet may also include intermediates and/or end products of 2-MEA or related aminothiols depending on the precursor used. The pellet was administered as is or, was re-suspended and washed at least once. The pellet was then administered to patients.

The living biological system is selected from the group consisting of yeast, lactic acid cultures, target cells, and other living cells. 2-MEA or related arninothiols and the living biological system were incubated between about 6 hours and about 72 hours depending on the type of living biological system. For example, yeast or yogurt cultures were incubated between about 6 hours and about 48 hours, lactic acid cultures were incubated between about 24 and about 48 hours, and target cells and other living cells were incubated between about 24 and 72 hours. The centrifuging step was performed from about 200 rpm to about 50,000 rpm.
Different centrifugation rates isolate specific components. Ultracentrifugation was sometimes employed after lysis of cell to recover and concentrate organelles and other fractions for use in the invention.

When 2-MEA and related aminothiols are combined with a living biological delivery system, the pellet can be administered to patients in several ways. First, the pellet can be orally administered. The pellet can be suspended in a yogurt medium and then applied topically to the skin of the patient. Further, the pellet can be lyophilized and then administered to the patient.

In another embodiment of the present invention, a therapeutic composition also called the complex formula is provided comprising therapeutic dosages of 2-MEA or related aminothiols, at least one antioxidant such as BHT, at least one transfer factor of the type developed by the inventor and disclosed herein below, and at least one living organism. Copper(II)-3,5 di-isopropyl salicylate may be included in the complex formulation in place of the 2-MEA or as an additional component. The 2-MEA or copper compound or the complex formula can inactivate and stabilize the presentation of the targeted condition, thereby minimizing the number of multiphasic steps needed in the neutralization of anticipated resistance.

In yet another embodiment of the present invention, a therapeutic composition and method is disclosed for using copper(II)-3,5 di-isopropyl salicylate in the treatment and prevention of AIDS, cancer, autoimmune diseases, and microbiological infections, comprising the step of administering an effective dosage of a therapeutic composition comprising copper(II)-3,5 di-isopropyl salicylate to a patient having AIDS, cancer, autoimmune disease, microbiological infections, and other diseases where immunological dysfunction and/or free radical formation function as part of the disease mechanism. The effective dosage of copper(II)-3,5 di-isopropyl salicylate for administration to a patient is between approximately 10 mg and about 500 mg, three times a day. Administration of the composition to a patient is accomplished in the same ways as previously described for 2-MEA, and is orally administered in the same forms as 2-MEA.

Like 2-MEA, copper(II)-3,5 di-isopropyl salicylate was combined with a living biological delivery system using the same method steps and same living biological systems as described for 2-MEA. Copper(II)-3,5 di-isopropyl salicylate and the living biological system were incubated between about 6 hours and about 72 hours depending on the type of living biological system. The pellet further included intermediates and/or end products of copper(II)-3,5 di-isopropyl salicylate. The centrifuging step was performed from about 200 rpm to about 50,000 rpm. Different centrifugation rates isolate specific components. Ultracentrifugation was sometimes employed after lysis of cell to recover and concentrate organelles and other fractions for use in the invention. The pellet was administered orally to the patient, suspended in a yogurt medium and applied topically to the skin of the patient, or lyophilized and then administered to the patient.

The therapeutic composition comprising an effective dosage of 2-MEA further includes an effective dosage of at least one antioxidant, wherein at least one antioxidant is selected from the group consisting of BHT, BHA, ethoxyquin, TBHQ, nordihydroguaracetic acid, lipoic acid, and vitamin C. The effective dosage of BHT for administration ranges between about 0.01 and about 2% of the dietary intake by patient weight.

The therapeutic composition comprising 2-MEA may further include an effective amount of at least one transfer factor in type and/or target. The effective dosage of the transfer factor for administration purposes ranges between about 1 mg and about 5 g per day. The transfer factor is selected from the group consisting of transfer factor of resistance, transfer factor of synergy, and transfer factor of anticipation.

The therapeutic composition may further include an effective dosage of living microorganisms selected from the group consisting of acidophilus, theophilus, thermophilus, *Lactobacillus bulgaricus, Lactobacillus plantarum,* yeast, kefir and rhizopus. One yeast that was used in the present invention was *Saccharomyces cerevisiae.*

DETAILED DESCRIPTION OF THE PREFERRED EMBODIMENTS

The present invention is directed to the use of 2-MEA and related aminothiols and copper(II)-3,5 di-isopropyl salicylate in the treatment of individuals with AIDS, cancer, microbiological infections and other immune deficient conditions as an adjunct to chemotherapy or radiotherapy, as a broad spectrum antioxidant substance for life extension, in combination with other compounds, or by itself. The effects of 2-MEA and copper(II)-3,5 di-isopropyl salicylate may be enhanced in combination with other compounds which function in one of several ways: 1) augment the effect of the compounds; 2) neutralize their side-effects; and/or 3) alter the targeted condition directly. For example, use of 2-MEA in combination with cimetidine (Tagamet®) or other comparable stomach pain relievers reduces the likelihood of ulcers commonly associated with the use of 2-MEA, an ulcerogenic compound. 2-MEA was also combined with certain antibiotics to neutralize the ulcerogenic side-effects of 2-MEA. Vaccination and antibiotics against heliobacter pylori and other ulcer-related organisms may be combined with 2-MEA to minimize ulcerogenic potential.

In augmenting the efficacy of 2-MEA, a wide range of antioxidants was used including but not limited to vitamins C and E, beta-carotene, supplements such as pycnogenol, selenium, germanium, nordihydroguaracetic acid, dimethyl sulfoxide, other natural or artificial antioxidants such as copper(II)-3,5 di-isopropyl salicylate, butylated hydroxytoluene (BHT), butylated hydroxyanisole (BHA), ethoxyquin, TBHQ, oxygen peroxide, folic acid or any antioxidant. The antioxidants helped to eliminate the free radicals, which are directly or indirectly generated by a number of disease conditions. These compounds in combination with 2-MEA and related aminothiols including penicillamine augmented the efficacy of 2-MEA in disease conditions, for example, AIDS, where 2-MEA and antioxidant activity was desired. In AIDS, part of the virus' generation is predicated on the virus using oxidized co-factors. Upon entering the cell, 2-MEA inhibits the co-factors from being oxidized, thereby preventing the virus from assimilating. Other antioxidants as listed above were found to enhance the effects of 2-MEA by enhancing its antioxidant effect.

Other factors that were found to augment 2-MEA's efficacy include intermediates and end products of 2-MEA and related aminothiols. The 2-MEA acts on cells, and then the intermediates were extracted from the cells. The 2-MEA was also added to target cells like skin cells, immune cells, etc. and then extracted from the target cells, thereby carrying the intermediates, activating factors, co-factors and other components which were activated by 2-MEA. 2-MEA has many functions, including one as an immune stimulator. A preferred method for using 2-MEA in a way that will enhance its immune functions upon administration to a patient is to use 2-MEA as well as its extracts from target cells. The extracts include genetic changes, enzymatic changes as well as activation factors. In other words, the present invention provides a method by which induced and amplified changes by 2-MEA are used to enhance the immunological and the antioxidant capacity of 2-MEA upon administration in vivo or in vitro to a patient or desired host system including animals.

The 2-MEA and related aminothiols including penicillamine were administered at all stages of the disease conditions tested at a dosage between about 0.01 mg and about 500 mg, at least daily up to 4 times daily. Depending on whether the activated target cells were human or animal origin and if you extract by injection or orally, 2-MEA dosages varied widely. When the 2-MEA acted on the target cells, the cells then produced genetic information for cellular multiplication and expansion. For example, 0.1 mg to about 100 mg or more of the transfer factor extracted from the activated target cells was an adequate daily dose to give patients.

It was also found that white blood cells removed from a patient and incubated with 2-MEA caused cellular multiplication. The incubated cells were then injected back into the patient The combination of the white blood cells and the 2-MEA produced a variety of extracts, transfer factors, precursors, etc. All of these products were capable of being administered back into the respective patients for treatment purposes. In the alternative, each of these products were broken down chemically, physically or biologically and the extracts therefrom were administered to the patients.

2-MEA may cause genetic, enzymatic, and other changes in the immune cells, which augment their efficacy and numbers. At the same time, 2-MEA may inhibit mutation and resistance in the targeted condition, for example, inhibition of viral replication in HIV.

Sparing function is unique to pharmacology, and is defined by the inventor as the optimal bioavailability and efficacy of a compound being facilitated by induction of secondary changes stimulated by the compound prior to its administration. To exemplify this, 2-MEA will induce cellular multiplication and changes on various levels of cellular function. A fraction of the administered dose is used in the induction of these changes, leaving less of the 2-MEA to carry out its primary and other functions in its original form.

Similarly, copper{II}-3,5 di-isopropyl salicylate will induce the formation of superoxide dismutase amongst other cellular changes. A fraction of the copper(II)complex will be used up in this induction, leaving less of the original form to carry out its primary antioxidant and other functions. Generation or creation of the induced change by supplementation of induced factors or their induction by genetic codes or factors such as transfer factors will minimize the amount of precursor eg.,2-MEA, copper(II)-3,5 di-isopropyl salicylate to be used in this manner and, thus have a sparing effect. Compounds may then maintain greater concentration and duration of action.

In yet another therapeutic approach to treating disease conditions like AIDS, cancer etc., 2-MEA was used in combination with other traditional medical therapies. Viral inhibitors dideoxyinosine (DDI), AZT, protease inhibitors, etc. and other agents combine effectively with 2-MEA as it affects viral replication at different sites. 2-MEA exhibited a very powerful multiplication, immunostimulating and immunomodulating activity. As a result, much greater efficacy against the virus was achieved with 2-MEA, leading to a rapid rise and normalization of T-cell parameters accompanied by a sustained drop in PCR. Lower dosages of drugs like AZT were required and much less toxicity occurred. Further, a much greater duration in the efficacy of the other therapeutic agents occurred in the presence of 2-MEA.

In the present invention, 2-MEA was combined with ozone, an oxidant. When ozone is at its maximum peak, 2-MEA is not; when 2-MEA is at its maximum peak, ozone is not. The rationale for the combination 2-MEA and ozone therapy is to have 2-MEA inactivate the intracellular virus so that the virus and the cells are prevented from dividing. Ozone, on the other hand, kills viruses in the bloodstream. The ozone is pulsed for a specific time period ranging from hours to days apart followed by 2-MEA therapy. Improvement was still observed when the modalities were used simultaneously, but interference also occurred. Each therapy is alternated so that 2-MEA is administered one day and the ozone therapy is given the following day. Ozone was administered by IV, orally, intramuscularly, by enema, etc. Blood tests were given at selected time periods to measure 2-MEA levels and oxidation levels. 2-MEA acts by entering the patient's cells and preventing the ozone from activating the virus. Viruses need oxidized components to grow inside cells. Ozone kills viruses in the blood. Ozone is capable of killing viruses outside the cells. The general idea with this combination therapy was to have an agent enter the cell while another agent killed the viruses in the bloodstream. This was achieved in several ways.

First, medial equipment like infusion pumps pumps blood into a chamber where it is ozonized, and then returned back into the patient's body. The inventor found that it did not matter how much 2-MEA was in the body, if you blast it with ozone, the viruses were killed. Ozone therapy and 2-MEA can also be combined and then pulsed into the body. Ozone therapy is currently one of the most common AIDS therapies. The ozone itself is inexpensive, but the procedure and equipment are quite costly. Moreover, ozone is effective for only a short period of time because of its toxicity. Almost everything that damages the body occurs when large amounts of free radicals are released. Ozone acts locally and spontaneously, so when the cells are protected by 2-MEA in the body, ozone produces damaging effects against the targeted disease without damaging the patient's normal cells.

In another embodiment of the present invention, the inventor developed a therapeutic kit, which combines a therapeutically effective dosage of 2-MEA in any form with an ozone preparation and a vaccine preparation. The 2-MEA offsets the ozone's damaging effect on the cells. 2-MEA augments the ozone damaging effect against the targeted disease. 2-MEA functions by augmenting the ozone effect not only against HIV, but also against other viral and microbial infections. 2-MEA amplifies the immune response which ozone by itself cannot achieve. While ozone may cause problems with vaccines by restricting some portion of the immune response and thereby damage the vaccine, adding 2-MEA to the vaccine protected it against the ozone's deleterious effects.

The addition of 2-MEA was found to augment the human immune response to the AIDS vaccine and, therefore, serves as a potential adjunct to immunotherapy for any viral or microbial disease. Injection of 2-MEA produced a more immediate and systemic effect, and caused less problems for individuals with ulcers by not passing through the stomach.

With chemotherapy, for example, the genetic information either protected white blood cells and the enzymatic information from the intermediates, and end products of the healthy white blood cells, can be used to selectively protect them, as opposed to 2-MEA which also protects the cancer cells. If amplified genetics are used, you might be able to protect the white blood cells without necessarily protecting the cancer cells because the genetic information would be translated by the cancer cells.

Transfer Factors and 2-MEA

Some transfer factors mentioned below and transformation factor are terms coined by the inventor. Transfer factors cause the activation of T-cells to attack the HIV. By raising a transfer factor against HIV in an animal system, that animal produces a simple transfer factor which causes the T-cells to increase in number and attack the HIV. Transfer factor can be raised against live HIV and trigger the immune system to attack the live virus. A transient increase in T-cells occurs and when they die, a drop in the T-cells occurs.

When 2-MEA is used in the patient, the viral structure will appear to change. You want to use a transfer factor of resistance or anticipation or transformation factors. Transfer factor of resistance involves taking a transfer factor, for example, from a horse which is resistant to AIDS, and add it to a test tube containing about 10,000 human or the patient's own T-cells. The AIDS virus is then added to the test tube. Of those approximate 10,000 T-cells which accept the transfer factor, most will attack the AIDS virus and die. However, some of the T-cells will accept a special part of the transfer factor of resistance, attack the AIDS virus and not die. Procedurally, incubate the surviving human T-cells having the transfer factor from the resistant animal with general human T-cells or even with the patient's own T-cells. Then culture the surviving T-cells because these cells have developed resistance to HIV. This step can be performed in one of two ways. One approach is to obtain more T-cells from the patient, incubate them with the transfer factor of resistance, and then administer them back into the patient. In the alternative, remove T-cells from pooled human blood, incubate them with the transfer factor of resistance, and then administer them to the preselected patients. In yet another approach, inject the transfer factor of resistance into an animal, and allow the animal to amplify the transfer factor. Next, extract the transfer factor from the animal's blood, and then administer the transfer factor into the patient.

A second type of transfer factor is transfer factor of synergy, and refers to the time period during which T-cells and PCR loads both rise in the patient's body. Over a period about 2–3 months, the PCR load and T-cells counts were examined by the inventor on a daily basis. Although prior to the present invention, it was believed that as AIDS patients started to deteriorate, T-cells went down and the viral load increased, the inventor found otherwise. In fact, in quite a number of conditions and several days a month, the relationship was just the opposite. In fact, the T-cells were found to increase as well as the PCR load. Similarly, the T-cells also decreased as well as the PCR load. Sometimes, the PCR decreased and the T-cells increased, or the PCR increased and the T-cells decreased. At times, studies showed the rise between T-cell counts and PCR counts almost parallel.

There were other times during the testing when the HIV virus and the immune system were both stimulated together. There were other periods when, despite viral stimulation, the immune system was not broken down. There was a phase during which synergy existed between the immune system and HIV. Certain infections caused the T-cell count to rise and the PCR load increase. These included certain colds and flus. There were influences that made the T-cells resistant to viral amplification's damaging effects. The virus would still grow in the T-cells but was unable to kill them.

A vaccine was duplicated which made the T-cells and the PCR increase together. Doubling of PCR would accompany similar increases in T-cell counts with certain staphylococcal extract vaccines. Certain phages of staphylococci could cause the T-cells to increase with variable effects on PCR. At the same time that the virus was growing, and when the T-cells and the PCR increased, these T-cells possessed a transfer factor of synergy. When this transfer factor of synergy was extracted out of the T-cells and incubated with the HIV virus or if a vaccine was used to raise them both together and incubated them with HIV, HIV still grew in those cells, but did not kill them.

A transfer factor of resistance does not allow for the amplification of the virus, so in vitro you do not get viral growth. On the other hand, transfer factor of synergy allows the virus to grow in harmony with the T-cells. The virus can divide in two ways. First, it can grow in the cell and cause it to explode. Secondly, it is believed that the HIV virus divides by budding off the T-cell membrane. The second option is compatible with cell survival.

A third transfer factor is transfer factor of provirus (TFP). In an experiment, T-cells from an AIDS patient were removed, amplified in a horse or chicken, and then readministered to the patient when his supply became depleted. The effect was very short-term. In yet another method, the TFP from these same white blood cells was amplified in an animal, and then readministered to the patient. When transfer factor is amplified, it is not known what type of transfer factor is produced as the end result. When the transfer factor was amplified and added to the patient's white blood cells in a test tube, the T-cells grew. Secondary amplification can then take place in vivo or in vitro.

Two things that are needed to cause a virus to go into a dormant state. One is for the virus to want to go into a dormant state, and the other is for the cell to force the virus to go into a dormant state. Viral specific factors can be isolated and cell specific factors can be isolated for a provirus state. A transfer factor was removed from the white blood cells and then amplified in an animal in vivo. The amplified transfer factor was then added to the animal's provirus T-cells in vitro. Transfer factor of provirus was added to non-infected T-cells along with HIV, and then cultured together. The inventor found that the T-cell count did not drop over 24–48 hours, and the HIV count did not increase or amplify either. Why is it that a transfer factor of provirus was involved rather than another type of transfer factor? When the white blood cells were stressed, the provirus became activated into a live virus and the mixture not only showed a high yield of HIV, but was also infective to other white blood cells.

There are three different but potent transfer factors, each of which can be used in combination with 2-MEA. For every beneficial transfer factor, there is an equal and opposite transfer factor (increased susceptibility, increased resistance, active viral phase). For every transfer that can help the human body and be actively safe, there is a transfer factor that can cause damage. An antiserum to the non-beneficial transfer factor would help to neutralize its negative effects.

A transfer factor extracted from a cell that is actively dying, for example, is a transfer factor of disease rather than a transfer factor of resistance. If 100 cells are infected with AIDS and most die, they release transfer factors of sensitivity, not transfer factor of resistance. If 100 cells become infected with AIDS and most survive, a transfer factor of resistance has been produced.

Transfer factor of sensitivity is used because one can alter the cells of the patient with transfer factor of sensitivity in vitro, then vaccinate the patient against that so that the cells never get a chance to multiply, expand or put out their transfer factor which will influence other cells. The sensitive part of the system can be stopped from being amplified. For every transfer factor that is good, there is a transfer factor that is deleterious. The idea is to isolate the negative transfer factor only to prevent it from generating and spreading to other cells.

Another type of transfer factor is curative transfer factor, which is transfer factor extracted from animals. Transfer factor from a horse is used because a horse is not susceptible to AIDS or HIV. If you vaccinate the horse against the targeted disease, remove the transfer factor and treat the patient with the horse transfer factor, the transfer factor will activate the patient's T-cells just the same way they did the horse, but the horse's T-cells are resistant to HIV and the human ones are not. They will attack the virus and die. The only way to make the transfer factor of the prior art viable is to use with the transfer factor of activity a transfer factor of resistance. One has to find the cells that will accept, not only increased activity from the horse, but also increased resistance from the horse. Unless cells are given amplified transfer factor of resistance, they will succumb to the infection.

Animal cells may resist HIV infection by virtue of superior immune function to human and/or by the lack of receptors to which HIV may attach and enter cells. As the second of these options gives animal cells inherent resistance not found in human cells, simple use of transfer factor from activated animal cells will induce greater anti-viral attack by vulnerable human lymphocytes and result in greater incidence of cellular infection. One way of preventing this outcome is by using transfer factor of resistance.

Another approach is to look for another cell type other than the targeted response cell, the T-cell. It is assumed that because the T-cells attack HIV, the T-cells need to be stimulated against HIV. But, animals do not have a first response against HIV with T-cells. Instead, their first response is with neutrophils. So whether we talk about AIDS or cancer, there is an initial response by an animal injected with neutrophils. Even in cases involving animals which do not respond with neutrophils, they can respond with other cells almost as effectively as humans do with T-cells. The further away one moves on the evolutionary scale from the human, the more varied the response against HIV. The lower you go on the animal scale and the further removed from the human being, the less likely you are to get anti-HIV activity of T-cells and the more likely you are to get neutrophils or T-cells, or whatever the animal's or fish's main immune response is. Even sharks have an effective anti-HIV system. The further the species gap, the less likely you are to respond. immunologically in the same way. That is a bonus because it means that if you go to a chicken, for example, you will not stimulate its T-cells. Instead, you stimulate neutrophils or B-cells and antibody-generating mechanisms. A totally new immune response can, thus, be activated in the patient.

AIDS patients have many neutrophils. They individuals have a large amount of neutrophils because the neutrophils are not attacked by HIV, and neutrophils are resistant to HIV. If you vaccinate an animal with HIV and it responds with a neutrophil attack, the transfer factor from the neutrophils can then be used to arm human neutrophils against HIV. What has been done is that part of the immune system is armed against the HIV virus that has not been seen before. But now that the transfer factor was used to activate it, the virus can be attacked by a part of the immune system that cannot succumb to the virus. These transfer factors are called curative transfer factors.

In carrying out the method of producing transfer factor and activating the immune system, a large amount of transfer factors were isolated from a horse against cancer cells, simply by injecting the horse with cancer cells. The immune response occurred with neutrophils within 3 hours following the injection. Extraction was usually performed within 2–3 weeks following the injection. However, if you wait this long, you actually miss the most effective transfer factor, which is produced about 3–6 hours after the first injection.

The isolated transfer factor can be used in several ways. First, you can activate the part of the human immune system designed to respond to HIV and, if you activate that part, you have to use a transfer factor of resistance to make sure that your new response is also resistant. In the alternative, you proceed to a part of the immune system that is not designed in the human to attack HIV, learn how to activate that part of the immune system in an animal, and isolate the animal's transfer factor.

A third option is to take a mixture of transfer factors of resistance, anticipation, provirus, synergy, neutrophils, T-cells, of early, intermediate and late response etc. from all the white blood cells in an animal and expose it to mixed white blood cells from humans or, even better, from the patient. If you add a mixture of transfer factors to the patient's blood from the animal and, instead of activating the T-cells, you activate the patient's blood cells, the patient's neutrophils will now attack the virus. Upon amplification of the transfer factor from the neutrophils, you produce an autogenous transfer factor which will cause a resistance of the cells that attack the virus. In yet another approach, transfer factors from all of the different cell types of are isolated and then exposed to different types of cells. Look for the cells which are not usually involved in the anti-AIDS process to develop anti-AIDS activity. There are three advantages of activating human white blood cells: 1) there are a lot more neutrophils than there are T-cells; 2) the neutrophil pool has not already been depleted by HIV; and 3) the pool is resistant to HIV.

Standard transfer factor manufacturing processes may be augmented by physical, chemical or biochemical stimulation of white blood cell division prior to the extraction process. Phages may cause amplification both before the extraction process and afterwards by at least stimulating division of responsive target cells. Phages stimulate amplification of the target cells, and will uptake and amplify the transfer factor. Phages may also extend the target cell beyond the Hayflick limit.

Transformation factors work differently than transfer actors. For example, you can produce transformation factors which are like a transfer factor from neutrophils which are capable of transforming T-cells into resistant parts of the immune system against HIV. In contrast to transfer factors, transformation factors are factors extracted out of one cell type that are capable of causing a change in another cell type. Neutrophils were used to extract transformation factors. Transformation factors will also transform target cells into resistant cells. In the present invention, transformation factor was isolated from white blood cells and used to activate red blood cells and from neutrophils to activate lymphocytes. Unlike transfer factors, transformation factors also have a strong capacity for being curative. The further down the specie level you descend from the human system, the more likely that transformation factors are being used instead of transfer factors, and the less likely one will encounter human analogs in the animals specie. In other words, the more primitive the animal, the more likely that a transformation factor is involved.

Anticipatory Transfer Factor

Anticipatory transfer factor has never been considered in the prior art to the knowledge of the inventor. It is useful because, for example, if you vaccinate a child against measles, mumps, or other childhood diseases, you have the risk of the child succumbing to a long-term side effect of the vaccine itself. The child may develop sub-acute sclerosing panencephalitis for example. Pretreating the patient with an anticipatory transfer factor against the vaccine will most likely achieve the following: a) minimize the time needed to develop immunity because of the prior exposure; b) may obviate the need for a living vaccine because the living vaccines are dangerous {you can use a killed vaccine if you amplify the immune response with transfer factor}; c) may even obviate the use of vaccines. The best anticipatory transfer factor is made of the patient's own cells. The best way to vaccinate someone with minimal risk is to remove their blood, expose it to the targeted agent, and then isolate the transfer factor from the mixture and re-administer it to the patient or mix autogenous blood with transfer factor and re-introduce into the patient.

While one may not be able to duplicate exactly what is going to happen to the patient by conducting in vitro studies, one may use an appropriate animal system to raise the transfer factor of anticipation. One problem is that animals do not become infected with the HIV to produce AIDS. A preferred system is to use the patient's own cells in vivo where they are exposed in a short burst to 2-MEA, the changed virus is isolated, and the transfer factor and transformation factors raised against the changed virus. The transfer factor is then administered back to the patient after about 1–2 days when the 2-MEA has washed out of his system. The result is vaccinating the patient against how the virus is going to look when 2-MEA is reintroduced into his system. Use the transfer factor and vaccine that was raised against the transformed virus for about 2–3 weeks when the immune response is adequate. Then start the patient on the 2-MEA.

To determine what the virus is going to look like, one could perform similar animal studies by administering 2-MEA to the animal, and then injecting it with normal HIV from the patient or from food. The problem, however, is that the virus will not enter the animal cells and will not create analogous changes. This applies equally well to other therapeutic compounds such as DDI, AZT, etc. As a better alternative, one can anticipate the changes that are going to be made in a patient by exposing the patient to short bursts of 2-MEA or the desired therapeutic composition or performing in vitro studies, vaccinate and raise transformation factor against the changes, stop the patient from taking the medication for a time period, vaccinate him against the changes, and then re-start the medication. The trouble with AZT and protein inhibitors is that you cannot start and stop them in this manner because it may induce viral changes, mutations or resistance. Furthermore, these drugs are not innocuous agents; they have their own side effects. A better approach is to keep these drugs in reserve and start treatment with an innocuous agent like 2-MEA first. After you elicit the maximum immunological response from 2-MEA and related aminothiols, and then administer 2-MEA in combination with AZT, then 2-MEA, AZT plus DDI, singly or in combination, to maximize the length of time of the anticipatory changes and the initiating therapy.

With 2-MEA, it is harder to induce a change because 2-MEA does not affect the virus directly like most other agents. 2-MEA affects the virus indirectly by optimal intracellular antioxidation of the cytoplasm, which prevents the membrane or outer wall of the virus from being built because viruses need oxidized co-factors. 2-MEA, therefore, affects the host cell more so than the virus itself, and the virus would have to adapt to a change in its environment to its host cell rather than to a direct attack. Viruses can respond better to a direct attack than to a change in the cell environment. The change in the environment also means that 2-MEA may not be able to prevent the insertion of virus into a cell, but it can prevent its proper replication in a cell, so 2-MEA exhibits a good preventative function.

There a number of ways in which to augment this effect by stopping the binding of the virus to the T-cell or whatever kind of cell. AL721 (lecithin extract) is one agent which makes the T-cell membranes more fluid. By itself, AL721 has not been useful because there is no such thing as a complete blockage so the virus can still bypass, enter and multiply in the cell. However, upon the addition of AL721 to 2-MEA, you have a blockage of entry and the blockage of multiplication upon entry. A combination of AL721, AZT,and 2-MEA provided a blockage of entry, a blockage of reverse transfer into the nucleus, and a blockage of multiplication. In essence, the more agents added, the more sites that were blocked effectively.

Therapeutic Agents which Offset the Ulcerogenic Effects of 2-MEA

Copper(II)-3,5 diisopropyl salicylate exhibits anti-ulcerogenic activity. It is a compound that can be used in an effective dosage of between approximately 10 mg and about 500 mg, three times a day. Copper(II)-3,5 diisopropyl salicylate is a compound which has dual efficacy having both an anti-inflammatory and some immune simulation capabilities. Generally, copper(II)-3,5 diisopropyl salicylate raises the level of superoxide dismutase, an intracellular enzyme which inhibits oxidation from taking place in the cell and may indeed function like 2-MEA. Copper(II)-3,5 diisopropyl salicylate has been largely researched for its inflammatory activity. The inventor found that copper(II)-3,5 di-isopropyl salicylate prevents the 2-MEA from being able to cause ulcers, and augments the intracellular antioxidation effect directly by raising the superoxide dismutase levels intracellularly. When using this compound in a preparation, a preferred method is to raise a transformation factor in anticipation of the changes in the formula with 2-MEA and other compounds.

Copper(II)-3,5 diisopropyl salicylate was used to treat an auto-immune disease where inflammation was a problem, starting with about 30 mg daily, divided into three doses of 10 mg. The capsule comprised about 10 mg copper(II)-3,5 diisopropyl salicylate, 200 g 2-MEA, 100 mg transfer factor, 100 mg BHT, and about 100–150 mg of AL721. Copper (II)-3,5 diisopropyl salicylate may be used by itself, in place of 2-MEA, in combination with traditional pharmaceuticals like AZT, BBI, DDC, etc., and as an adjunct to all other therapies for inflammatory diseases, malignant diseases, infectious diseases, etc. Penicillamine is used to pull out excess iron from the body. There are prescription items only, whereas 2-MEA is probably available in the stores.

Mutation inhibition factors and reactivation inhibition factors are defined as any factor which prevents a virus from mutating. By definition, this includes most of the above except that conventional therapies actually promote viral mutation. One way the virus mutates is by marriage with and cannibalism of cellular structures, microorganism structures, and perhaps other viral structures in the system. Two things can occur if a major virus like herpes or shingles gets into the system. The herpes virus may either be reactivated by it or it may be mutated by it. One way to avoid this is to use a broad spectrum of preservatives antiseptic antibiotics. BHT has a large LD50, has been be used for a long time, and is generally considered a safe product BHT augmented the antioxidant capacity of 2-MEA intracellularly and prevented additional infections, several microbial and viral infections, which would in turn control the infection that would mutate or activate the virus. To optimize BHT's activity, BHT should be combined with other microorganisms or a living biological system. This is essentially a mixture of microorganisms that cannot colonize the patient's intestine but prevent infections from coming in. These microorganisms can also be inhaled to protect your lungs and others may be rubbed onto the skin. Having a known set of microorganisms colonizing the body or monopolizing the body makes it harder for the virus to mutate in a form that you can anticipate. A range of microorganisms will colonize and stabilize the microflora and prevent antigens from activating the virus through the draining of the immune function or super added infection and prevent a mutation of the virus.

The changes in transfer factor of synergy are not just changes that happen to the cell. The changes occur to the virus too. Two closely related viruses will always interfere strongly with each other. For example, you cannot infect bacteria with a phage and then infect it with a similar phage. One way to protect T-cells against a mutated HIV is to actually infect those T-cells with a pro-virus form of HIV. If you extract out the virus from the patient when it was not breaking up his T-cells, and then inject it back into him when it is breaking up his T-cells, his own mutants of virus will compete with each other for the T-cells.

One way to slow down the T-cell breakdown is to re-infect the patient with the original strain which he was coping well with. The original strain will compete with the mutant strain for the receptors on the cell. Once the old strain attaches to the cell, the antibodies formed will be able to destroy it. It is a way of therapeutic insertion or of constantly keeping the virus competing with its old form. It is a way of reversing the tide of mutation.

When you extract out virus from a pro-virus stage, cells synergize with the virus and have difficulty being destroyed by more aggressive forms of the virus because the virus already in them is protecting them against the more aggressive one.

Levamisole, interferon, interleukin or any immune stimulants can all work in this formulation. Once there is the transfer factor of anticipation, use can begin on the conventional therapies for AIDS which include immune stimulants which include all the other agents because, in the past, immune stimulants only caused a temporary and transient change that would pass and leave the patients in a worse state. You could use interferon and interleukin to stimulate the AIDS patient, have the T-cells show greater numbers, and then the person dies because he used up his reserves. With transfer factors of anticipation, resistance and transformation factors, when you stimulate the immune system, it will be a different system, one that is resistant to the disease and one that can anticipate the damages. You can now start using immune stimulants as well, and these will all fit into the formulation. The preferred composition of this invention is the combination of 2-MEA, transfer factor, BHT, and living organisms in a single dosage.

Penicillin and penicillamine also have short-term activity against HIV. Very high dosages of penicillin may actually help in the treatment of AIDS patients temporarily. The preferred culture techniques are techniques where organisms are made to compete for nutrients and/or one or more organisms are forced to use other organisms in culture for nutrition and/or when such nutrition is deficient in the medium and/or where one or more of the organisms is selected for by provision of its optimal needs. These can be used to develop microorganisms whole, part, or extract thereof with specific activity against targeted condition or organism. It is, therefor, possible to produce a penicillin with strong anti-HIV activity. Anticipatory vaccines against other infections which occur with AIDS can also be added to this formula. Preferred culture techniques include living cells such as human and/or autogenous lymphocytes, fibroblasts, etc. which may be used in whole, part or extracts thereof.

Other Immunostimulating, Immunomodulating, Inductors/augmentors of Normal Cellular Function Coenzyme Q10 is a powerful antioxidant, a mitochondrial antioxidant and entrocytoplasmic, which enables it to synergize with 2-MEA and copper(II)-3,5 diisopropyl salicylate and BHT. Coenzyme Q10 is also an immune stimulant.

Reishi mushrooms or shitake mushrooms from health food stores all have some immune stimulatory function. The anticipatory, mutation inhibition factor and antioxidant ability mixed with 2-MEA should be part of the invention. All major vitamins and minerals, transformation factor, methionine, selenium, chromium picolonate, growth hormones should be added amongst many other factors.

Micrococcus extract is very powerful against AIDS. Living organisms are biological enhancement factors.

T-8 cell is the suppressive cell; T-4 cell is the help cell. T-8 counts usually raise very high in AIDS patients; the T4 counts plummet. T-8:T-4 ratio should be a little above 1 in normal conditions.

If the therapy is given within proximity of the radiotherapy and chemotherapy, it may negate the effects of the chemotherapy and radiotherapy because it is a powerful antioxidant. Time for administration would be 2 weeks after the chemo is given; 2–3 weeks after radiation is given. It may also raise the tolerance level of the body so you can use more chemotherapy and radiation. 2-MEA and other powerful antioxidants and other anti-cancer agents such as bleomycin are more active in reduced oxidized state. The chemo goes into the body, oxidizes, kills the cells, and then the 2-MEA pushes it back into reduced state, so it becomes toxic again. Parts of this formula may aggravate some chemotherapy toxicity. Smaller doses of chemo can be given by constantly reactivating it. Instead of giving bleomycin in huge doses that cause hair to fall out, you give 2-MEA and it will reactivate the bleomycin originally given.

Living biological system is a mixture of organisms isolated from food, but which coexist together which can synergize together and which can come into a steady state of harmony. So all of these go into the stomach and grow into an ecosystem, which is a living biological system. This is part of the 2-MEA formula or the microbial environmental stability factor. You know what the microbes will be. Living biological systems alone have an interference action with HIV and HIV co-factors and are good stimulants. They are part of the formula yet need to stand on their own. They would also help prevent ulcer formation. Lactic acid bacteria (acidophilus), kefir, and rhizopus are safe, non-pathogenic organisms in a mixture whereby each, as a unit or in combination, donate beneficial features to the whole host and/or where they exist in an ecosystem which prevents superadded infection to the infiltration of the host by pathogenic organisms. The organisms and strains chosen for this living biological system have specific capacity for mediating anti-cancer activity and cholesterol lowering activity, as well as organism maintenance activity. The difference between living biological systems and prior art, where prior art is the administration of several strains of acidophilus, for example, or mixtures of up to 6–10 different organisms, is that a living biological system by its source and nature generally comprises more than 30 organisms. In fact, the more organisms involved in the living biological system is usually the greater stability and duration of action and the greater spectrum of activity. Being isolated from food sources, natural kefir, for example, can compose thousands of organisms, and a living biological system, in its optimum state, would combine several hundreds of organisms to best offset infection and to function best as a community.

Prior art consists of acidophilus, for example, in capsules, chosen for its purity and color, whereas in nature nothing exists like that. Living biological systems described here are unique in a) the combination; b) the number of organisms; c) the location of the organisms. There is no other therapy which seeks to occupy structures other than the intestines, for example, of living biological systems. These can also be inserted as a nasal spray for nasal sinuses and lungs, where a living biological system can comprise viruses, bacteria, fungi, etc. For example, in the immune compromised state, phages for various bacteria can be assembled as a living biological system and inhaled on a daily or weekly basis to prevent infection with said bacteria. The living biological system as described herein may be defined by its constituents or may be defined by the activity of the constituents. For example, a virus, bacteria, fungus and yeast which carry anti-cancer activity could be combined into an anti-cancer living biological system. Living biological systems may exist whole or processed such that they are lysed so that whatever internal enzymatic factors may be released into the system. They can also be formulated to target specific sources and their internal nutrients can do the same, and a living biological system can be formed which would be a constant producer of by-products. For example, organisms which are capable of manufacturing vitamin C can be orally administered once a month and would continue to produce the said vitamin in body for the duration of the month. Living biological systems make it possible to insert replicating forms of enzymes so that it is taken only once a month or once a year.

Living biological systems may be used as mutation imagery factors and reactivation inhibitory factors. One of the most powerful vaccines is the insertion of a dead feline panleukopenia virus into the blood stream of an AIDS patient. It may be because HIV functions as a hybrid of feline panleukopenia virus and hepatitis. HIV will function like a mixture of these two viruses. If you vaccinate against the function that is composed of two different things, and you upset the equilibrium by adding more of one, you disrupt the structure. HIV does not look like a simple hepatitis fused, but the theory is there. It is similar to disruption or vaccinating against something against the mechanism. Feline panleukopenia virus causes destruction of leukemia of white blood cells, as does AIDS. Vaccinating against feline panleukopenia virus somehow also vaccinates against its destructive capacity, and it is similar to the AIDS destructive capacity. Once you have vaccinated the body against one, the other also follows. There are a line of vaccines which are developed which do not attack the cause, but the mechanism. Smallpox and vaccinia are similar viruses so you can use one to immunize against the other. Bacterial phages and HIV are in no way similar, except that they can attack a cell, insert themselves into it, and cause the cell to die. You can use phages to vaccinate against AIDS. You can use feline panleukopenia virus, which can affect the white blood cells and kill it, against AIDS. An AIDS infected immune system will still act against feline panleukopenia virus, and it induce cell death in only a certain number of ways, and there is an overlap between what is used by the FPLV and the HIV. You can push the HIV into a dormant state to stop it from killing the cells by vaccinating against PLPV. The thing they have in common is the release of the death sequence, so that by vaccinating against one, you prevent the formation of death sequence which prevents the other from functioning.

The third observation is that a living feline panleukopenia virus may not have any greater effect than a dead feline panleukopenia virus. The reason is that the living one may cause some harm to the immune system and can overcome it. Whereas a dead one will only be reactivated at the site of viral activity. If you put in a fragmented virus where a virus is actively growing, even if it is another virus, a dead virus can use the first virus's growth mechanisms to reassemble itself. If you inject feline panleukopenia virus into a body that is infected with AIDS, only the cells infected with AIDS, which have a system for growing and structuring viruses, can absorb the feline panleukopenia dead and reassemble it. Novine virus shows up in every AIDS-infected cell—and only in every AIDS-infected cell. The body can identify that and can attack it and destroy it. Particularly if the virus being used to reactivate has foreign graft antigens from the same species or different species. The AIDS-infected cell now looks like a foreign cell from another source. Furthermore, specific antisera may be used against the reactivated virus and the complex that it forms.

Once reactivated, 2-MEA can hold that reactivated virus, so you can vaccinate against it, raise transfer factors against the reactivated virus, use 2-MEA to hold the situation as status quo until the immune system can build up and attack it.

2-MEA can be delivered by cell targets, by liposome and by agents to be uptaken by the target. For example, in the case of leukemia, if you want to place the 2-MEA in the normal cells but not leukemia cells, you would incubate the 2-MEA in culture with a bacteria which your body is likely to attack. Kill the bacteria and inject it into the membrane which is saturated with 2-MEA into the body. The normal white blood cells would attack it and absorb the 2-MEA, whereas the cancerous white blood cells would not respond to it. This will get 2-MEA specifically into a site where you want it. You can use any of the various ingredients.

Clinical Examples of Efficacy
An AIDS Patient—28-year-old Male
Lethargy, low T-cell count—200
T4/T8 ratio—0.24
Following 4 weeks on 2-MEA at 200 mg three times daily orally. Moderate increase in energy levels; T-cell count— 350. T4/T8 ratio was 0.5.

An AIDS Patient—48-year-old Male
Diarrhea, pneumonia (pneumocystis)
T-cell count—8
Treated with 2-MEA at 200 mg TDS
Copper(II)2,3,5-di-isopropyl salicylate was administered 10 mg daily. BHT was administered 600 mg per day. Living biological culture systems/cell extracts at a dose of 10 g TDS—membrane/enzyme and other living biological system components from organisms (non-pathogenic) found in food and from organisms that include lactobacilli, acidophilus, bulgaricus, bifidus, thermophilus as well as kefir and various rhizopii, at 300 million organisms per mg. After three days of treatment, there was resolution of the diarrhea. The pneumonia subsided in 1 week (patient was also on antibiotic therapy). The patient's T-cell count after 4 weeks was 60.

An AIDS Patient—59-year-old Male
Patient presented with Kaposi's Sarcoma involving both extremities which was very painful. The T-cell count was 120 and the T4/T8 ration was 0.6. The patient was treated with 2-MEA, 200 mg TDS. The patient was also given copper(II)-3,5-di-isopropyl salicylate, 10 mg TDS; BHT at 600 mg daily; living biological system as in the previously mentioned case; Also micrococcus sp and extracts were used. ATPIUTP/GTP—10 mg each orally daily; multiple nutritional supplement base including enzymes, antioxidants natural and artificial, etc.; KREBS cycle nutrients; enzymes; and cofactors. Following treatment, the pain disappeared in 2 days. Energy levels increased within 24 hours. Within 3 weeks, the T-cell count was 400 and T4/T8 ratio was 1.2. Further, shrinkage of Kaposi's lesions was observed.

Prostate Cancer with Bone Metastasis in 69-year-old Male
Complex formula as in previous case involving a 59 year old male was used. Pain decreased within 6 hours. Immunological parameters also improved within 3 weeks.

Complex formulation suspended during radiotherapy. It is theoretically possible for this therapy to interfere with chemotherapy/radiotherapy or any other treatment which acts at least in part by the generation of free radicals. By use of specificity and targeting patent technology by the same inventor, benefits of the formulation such as antioxidant ability, could be directed to healthy cells, for example, and away from diseased cells, without use of that technology, however, or selective delivery of precursors, intermediates or end-products, then one needs to observe the caution mentioned. This, however, covers the use of any or all of the ingredients in the recovery from toxic effects of treatment including those of chemotherapy and radiotherapy. As previously mentioned, unless precise targeting is available, it is better to use the antioxidant part of the formulation following the toxic therapy and not simultaneously. Living biological systems as complicated as those mentioned here and as simple as those of acidophilus and other yogurt cultures are being patented here for use solely or in combination with other factors, agents and products thereof in the prophylaxis and treatment of the side-effects of chemotherapy and radiotherapy. It is easy to see how living systems such as those can prevent bowel flora imbalance as can be caused by such therapy and how this ability, as well as the ability to prevent opportunistic bowel infections which may follow diarrhea and/or immunosuppression precipitated by the therapy, may be beneficial. There are other mechanisms at play here, including immunostimulant properties and other anti-disease factors inherent in or inducible by the appropriate living biological systems.

Post radiotherapy, the patient was recommenced on the preparation. All malaise and nausea resolved in three days. White blood cell counts which had dropped below half normal to normal levels in four days.

Ten patients were administered the complex formulation as above at one-third the normal dose, and were matched for age/sex and stage of disease. The supplemented group tolerated chemotherapy and radiotherapy with minimal side effects. Superior response and clinical condition of supplemented group was not only evident subjectively but objectively, also in that the control group repeatedly demonstrated lower immunological parameters, required more transfusions and almost double the number of days hospitalization as the group receiving the supplementation over a two-year follow-up.

There were eight deaths in the control group to only four in the supplemented group.

Twenty AIDS patients with T-cell counts 400–500 were divided into two groups. Ten patients were supplemented, the other ten availed themselves of whatever therapy they had available. After a 6-year follow-up, all unsupplemented group had died; six of the ten supplemented were still alive.

Improvements have been noted in multiple other conditions including arthritis, multiple sclerosis, cardiovascular disease, asthma, chronic fatigue syndrome, systemic lupus erytheromatosis, autoimmune disease, acute and degenerative diseases, infections, among others.

There are multiple applications relating to the immunopotentiating, antioxidant and ulcerogenic activities of 2-MEA and related aminothiols that may be of use. This invention covers the use of such compounds in any condition where neutralization of free radicals may play a beneficial role. This patent also covers the use of anti-ulcer and preventive medication/compounds/therapies in combination with 2-MEA. Use of 2-MEA and related aminothiols in combination with copper(II)-2,3-di-isopropyl salicylate could fulfill the requirements of an ulcerogenic with the added benefits bestowed by the anticancer, antiviral, antioxidant and other properties of copper(II)-2,3-di-isopropyl salicylate.

Biopharmaceuticals

A new line of therapeutic/preventative and supplemental products where a pharmaceutical agent is bound to an infection with affinity for target organism/cell where the biological agent or fragment thereof is used for specific delivery to target; to optimize concentration of agent at target; to process the agent so as to produce useful precursors intermediates and end-products; and to augment directly or indirectly the effect required. Biological delivery mechanisms may also be used to minimize irritant or other side effects of therapeutic agents.

1) Minimizing Side Effects

2-MEA and copper(II)-3,5 di-isopropyl salicylate can both cause local irritant effects in therapeutic levels. 2=MEA has been known to cause ulcer formation. Copper(II)-3,5 di-isopropyl salicylate is topically irritant. When placed into a biological carrier (inert such as liposomes benefit may be obtained from improved efficiency of absorption and perhaps preferential distribution; binding to targeting agents has been in prior art largely reserved to the use of monoclonal antibodies; the problem here has always been one of disassociation of antibody-pharmaceutical complex and of the targeting mechanism being restricted to the delivery of agent at the superficial membrane site.

Whereas the concept of biopharmaceuticals includes the use of monoclonal antibodies to deliver not only therapeutic but also preventative and other agents to the target tissue (prior art covers delivery to diseased tissue); current art provides for delivery of protective and other desirable agents to healthy tissue and/or to diseases other than cancer which is the centerpiece of prior art.

A major variation on prior art in the use of biological mechanisms is not restricted to biological amplification and processing pathways but involved the use of antigens rather than antibodies in the preferential delivery mechanism.

2) Antigen Delivery Mechanism

Various antigens have the capacity to bind directly to the target cell or tissue either by affinity or by virtue of prevailing conditions within the vicinity and structure of the tissue to be targeted, e.g., lymphopoietic tissue may be targeted b viruses such as mumps virus or feline panleukopenia virus. Any biological/chemical or physical agent incorporated in this living system or part thereof will automatically be carried to target. Chemotherapeutic agents may be carried to tumor masses including the use of anaerobic or microaerophilic organisms to deliver chemotherapeutic agents in high concentration to the center of tumor masses. An example to be outlined serves to demonstrate this amplification technique as relates to immunostimulants.

Prior art in vaccination relates to the use of non-specific adjuvants such as that of Freunds along with vaccine to be given or the use of interferon, interleukin, etc. Prior art does not include direct targeting or amplification technology.

An antibody needs to go after receptors whereas biopharmaceuticals go after prevailing conditions. An antibody to cancer needs the cancer cell to express the antigen. Biopharmaceuticals may go after a condition ie., lack of oxygen in the center of a cancer mass. If an organism is anaerobic or microaerophilic and you saturate it with a pharmaceutical, or supplement or a genetic sequence, then the organism will go to where there is no oxygen and deliver its payload. An example of the mechanism of action of biopharmaceuticals is presented below.

A microaerophilic or aerophilic organism in 500 cc of trypticated soy broth in the presence of a radioactive isotope, $I^{131}$. Incubation and fermentation occurred over a 2–3 day period. The organisms were filtered through a filter membrane, for example a 0.2 micron filter. The filtrate was re-suspended and washed in normal saline. The filtered fraction was re-constituted to a concentration of 10 million organisms per 1 cc. 1 ml was injected into a rate bearing Morris TC hepatoma. Following 24 hours, radiation was detected at the tumor site. After 48–72 hours, necrosis was seen at the tumor site.

In other experiments, staphylococcus aureus is incubated in a medium of trypticated soy broth for 24 hours. Medium also includes 5 mm of 2-MEA. Identical preparation is made without the 2-MEA. 100 cc of inoculated broth is then passed through a 0.2 micron filter. Pellets deposited on the filter are resuspended in 10 cc of normal saline then refiltered and resuspended. Both a suspended in 10 cc of normal saline and 5 mm of 2-MEA and the full 10 cc are injected into each of two horses. White blood cell are collected at 3 hours, 24 hours and 14 days. Crude transfer factor extract was prepared by freezing, thawing and 0.2 micron filtration of 100 cc of white blood cells suspended in normal saline at concentration of ten million cells per cc.

One cc of transfer factor was fed to Balb C mice every day for 10 days followed by bacterial cell challenge. One cc containing 10 million organisms of the original staphylococcus lethargy was noted for 1–3 days but no abscesses developed. Control group of 10 mice was inoculated intramuscularly. These were evaluated after 10 days. Six of the mice developed abscesses locally. All demonstrated lethargy for several days after inoculation.

The suggestion that the transfer factor was more effective from the horse treated with the 2-MEA suggested a specific stimulation of appropriate cellular response. When 2-MEA was combined in solution with the bacterial preparation immediately prior to inoculation of horse, transfer factor demonstrated no marked increase in efficacy, although transfer factor yield may have been greater than the control yield.

Incorporation of 2-MEA and other immunostimulants into the cells or organisms to be targeted or against which an immune response needs elicitation including bacterial, viral and malignant cells among others may lead to superior vaccines.

An extension of this invention is the feeding of transfer factor in culture preparation of vaccine and/or provision concomitantly to increase efficacy of therapy.

Copper di-isopropyl salicylate can induce production of superoxide dismutase. Preincubation with a biological delivery system such as living human/animal cells or various microorganisms such as yeast will enable not only targeted delivery of the compound but can also generate superoxide dismutase and/or other antioxidant enzymes as active factors. Biological active factors may be amplified by exposure to an oxidant such as 2% peroxide. Following generation of antioxidant enzymes, the peroxide may be neutralized by antioxidants such as vitamin C. In all the above cases, targeting complex may be used whole or in part, living or inactivated by physical, chemical or biological agents such as ultrasound, phenol or enzymatic degradation.

Use of biological delivery mechanisms also enables the topical application of such products for cosmetic, protective and other effects. One modality of application involves the absorption, activation and application of 2-MEA and copper di-isopropyl salicylate into target cells such as yeast or lactobacilli or human cells with 2-MEA and grown into a culture. Human cells and/or autogenous cells of skin, blood or other source may be cultured in vitro and suspended live or killed in a cosmetic base or yogurt base. Culture techniques may dedifferentiate cell types and/or may be used to stress the cells or manipulate in other ways to produce antioxidant and other beneficial enzymes and factors. Manipulation of temperature will yield to factors protective against heat and cold, as well as moisture loss, if that is made a condition of culture. Following stress, cells may be returned to friendly antioxidized environment to reduce free radicals. Cells are then disrupted or fixed so as to maintain all beneficial factors and not allow for their return to original parameters. In living or dead state, such cells will maintain genetic and other response modalities which may prove beneficial as therapy/prevention/supplementation or topical application to recipient. Various donor systems may yield beneficial properties but autogenous cells which have been manipulated or augmented in a physical/chemical or biological manner enable greater interaction and protection of recipient.

Cells suffer radiation damage, for example, when exposed to frequencies that are absorbed by vital cellular fractions such as the DNA and those structure are damaged. It is possible to evaluate the sites most frequently damaged and prepare a topical concentrate of the same or similar structures to shield the body. It is also possible to anticipate the exposure and make preparations from cells that service such exposure to confer protection and it is possible to use the whole cell, genetic fractions or other fractions to confer the resistance. Autogenous cells, however, provide the best matching of DNA and other susceptible fractions. Addition of 2-MEA to the culture media can increase their resistance to radiation and other factors, thus providing for greater shielding. Copper(II) 3,5 di-isopropyl salicylate and other antioxidants may also similarly be used.

Autogenous cosmetics can also include immune cell amplification from blood used a cosmetic to combat pimples. Again, this invention covers the concept of the use of living systems or fragments thereof to provide shielding or protection against particular challenge or disorder. Autogenous cells ensure minimal allergic responses, improved efficacy and bioavailability. Use of 2-MEA and related aminothiols and/or copper(II) 3,5 di-isopropyl salicylate and other di-isopropyl salicylates, as well as other factors, may amplify and augment efficacy.

The use of such preparations particularly autogenous may shield normal cells from radiotherapy by coating the outside of the body with counterparts which have been augmented and/or amplified to receive harmful frequencies, whether on the body or fixed in a shield/filter between the beam source and the body. Normal structures should be spared at least some damage and optimal damage to disease-specific structures achieved. With biopharmaceuticals, the agent can be processed and presented to the body in a more effective form such as precursors, intermediates and end products.

Certain modifications and improvements will occur to those skilled in the art upon a reading of the foregoing description. It should be understood that all such modifications and improvements have been deleted herein for the sake of conciseness and readability but are properly within the scope of the following claims.

I claim:

1. A method for treatment and prevention of sarcoma, including AIDS-related sarcoma, said method comprising the step of:

orally administering between about 200 mg and 500 mg of an immunoregulatory and antioxidant therapeutic composition which simultaneously stimulates and suppresses the immune system, said composition comprising substantially purified 2-MEA to a patient having sarcoma, including AIDS-related sarcoma.

2. The method according to claim 1 wherein the effective dosage of 2-MEA or said related aminothiols is administered at least one, and up to four times a day.

3. The method according to claim 1, wherein the therapeutic composition is administered to a patient by a means selected from the group consisting of oral administration, catheter administration, intramuscular administration, intravenous administration, intradermal administration, intradural administration, intravesical administration, intraurethral administration, intrathecal administration, inhalation, topical administration, sub-cutaneous administration, rectal administration, and any other administration means.

4. The method according to claim 3, wherein the composition is orally administered in a form selected from the group consisting of a capsule, gel cap, liquid, tablet.

* * * * *